(12) United States Patent
Adams et al.

(10) Patent No.: US 6,514,961 B1
(45) Date of Patent: Feb. 4, 2003

(54) AZETIDINECARBOXAMIDE DERIVATIVES FOR THE TREATMENT OF CNS DISORDERS

(75) Inventors: David Reginald Adams, Wokingham (GB); Ian Anthony Cliffe, Wokingham (GB); Howard Langham Mansell, Wokingham (GB); Nathaniel Julius Monck, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 10/091,346

(22) Filed: Mar. 6, 2002

Related U.S. Application Data

(63) Continuation of application No. 09/600,629, filed as application No. PCT/GB99/00224 on Jan. 22, 1999, now abandoned.

(30) Foreign Application Priority Data

Jan. 23, 1998 (GB) .............................................. 9801501

(51) Int. Cl.⁷ ..................... A61K 31/397; C07D 205/04
(52) U.S. Cl. ................... 514/210.01; 548/952
(58) Field of Search ..................... 514/210.01; 548/952

(56) References Cited

U.S. PATENT DOCUMENTS

| 4,226,861 A | 10/1980 | Cale, Jr. ...................... 424/244 |
| 5,068,231 A | 11/1991 | Taylor, Jr. et al. .......... 514/210 |
| 5,183,903 A | 2/1993 | Welstead, Jr. et al. ...... 548/952 |

FOREIGN PATENT DOCUMENTS

| EP | 0 102 740 | 3/1984 |
| EP | 0 194 112 | 9/1986 |

*Primary Examiner*—Joseph K. McKane
*Assistant Examiner*—Sonya N. Wright
(74) *Attorney, Agent, or Firm*—Foley & Lardner

(57) ABSTRACT

A compound of formula (1):

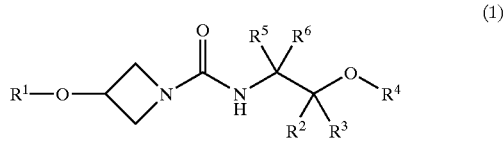

(1)

wherein $R^1$ is aryl; and $R^2$, $R^3$, $R^4$, $R^5$ and $R^6$ which may be the same or different are selected from H, alkyl and aryl; pharmaceutically acceptable addition compounds thereof and the use of the compounds in therapy, particularly for CNS disorders such as anxiety and epilepsy.

29 Claims, No Drawings

AZETIDINECARBOXAMIDE DERIVATIVES FOR THE TREATMENT OF CNS DISORDERS

This application is a continuation of Ser. No. 09/600,629 filed Sep. 8, 2000, now abandoned which is a 371 of PCT/GB99/00224 filed Jan. 22, 1999.

The present invention relates to chemical compounds useful in the treatment of disorders of the central nervous system (CNS), such as anxiety and all forms of epilepsy, particularly in humans. The invention also relates to the use of such compounds, pharmaceutical preparations containing such compounds and to methods of preparing such compounds.

Anxiety disorders affect an estimated 73 million people world-wide. The benzodiazepines have provided the dominant therapy for anxiety over the past three decades and there is no doubt that they are remarkably effective anxiolytics. However, chronic administration of benzodiazepines produces severe dependence liability, withdrawal syndromes, and side effects (sedation, amnesia, muscle relaxation). The only non-benzodiazepine anxiolytic that has been launched over the past decade is the 5-HT receptor ligand buspirone (Buspar®). This drug has had a remarkable commercial success despite being regarded as a weak anxiolytic (compared with the benzodiazepines) and having a long latency to onset of therapeutic action (2–4 weeks). In addition, buspirone and all related 5-HT$_{1A}$ partial agonists suffer from a dose-limiting side-effect profile comprising nausea, vertigo and endocrine changes.

The aetiology of anxiety disorders is not fully understood, but it is now established that benzodiazepines act by potentiating GABAergic neurotransmission although there is strong evidence that other neurotransmitter systems are modulated indirectly—in particular, the serotonergic and noradrenergic systems. Many pharmaceutical companies have invested considerable resource into the development of serotonergic anxiolytics. However, it is now apparent that ligands selective for 5-HT receptor subtypes, despite displaying anxiolytic-like activity in a restricted range of anxiety models, have, at best, very weak and/or non-dose-related anxiolytic effects in the clinic. The 5-HT$_3$ receptor antagonists are now discredited as psychotropics: they have a restricted range of activity in functional and anxiety models; they show no convincing anxiolytic effects in the clinic; and they are now accepted only as useful anti-emetics. The 5-HT$_{2A}$ antagonists similarly are regarded as ineffective in terms of psychotropic activity. The clinical utility of 5-HT$_{1A}$ receptor agonists and partial agonists is severely limited by their intrinsically weak action and by the dose-limiting side-effects (vertigo, endocrine changes, nausea) which become more intense as the agonist efficacy of these molecules is increased. The selective CCK$_B$ receptor antagonists have displayed an unimpressive preclinical profile similar to that of selective 5-HT ligands such as the 5-HT3 antagonists.

Serotonergic anxiolytics include the selective serotonin reuptake inhibitors (SSRI's) which, in addition to displaying antidepressant properties, are also effective in anxiety disorders such as panic disorder and obsessive-compulsive disorder. However, as with their antidepressant action, the major drawback with these compounds is the long delay (6–8 weeks) in the onset of clinical improvement following chronic administration.

A strategy in recent years towards improving the clinical profile of classical benzodiazepines is that of developing benzodiazepine receptor partial agonists, according to the rationale that they would have a more selective anxiolytic action and be less liable to induce dependence. However, this approach appears to have failed owing to the very weak anxiolytic actions of these compounds and their poor side-effect profiles (there is either a low or non-existent ratio between anxiolytic and sedative doses).

U.S. Pat. No. 4,956,359 and EP-A-0194112 disclose 3-aryloxy and 3-arylthio azetidinecarboxamides and their anti-convulsant and anti-epileptic activity. However, these compounds, like the benzodiazepines, have low water solubility which leads to difficulties in formulation.

There remains therefore a need for novel anxiolytic and anti-epileptic agents which do not suffer the above-mentioned drawbacks.

According to the present invention there is provided a chemical compound of formula (1)

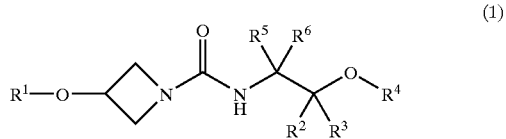

wherein:
R$^1$ is aryl; and
R$^2$, R$^3$, R$^4$, R$^5$ and R$^6$ which may be the same or different are selected from H, alkyl and aryl;
and pharmaceutically acceptable addition compounds thereof.

Reference in the present specification to an "alkyl" group means a branched or unbranched, cyclic or acyclic, saturated or unsaturated (e.g. alkenyl (including allyl) or alkynyl (including propargyl)) hydrocarbyl radical. Where cyclic or acyclic the alkyl group is preferably C$_1$ to C$_{12}$, more preferably C$_1$ to C$_8$ (such as methyl, ethyl, propyl, isopropyl butyl, isobutyl, tert-butyl, amyl, isoamyl, hexyl, heptyl, octyl).

Reference in the present specification to an "aryl" group means a mono or bicyclic aromatic group, such as phenyl or naphthyl.

The alkyl and aryl groups may be substituted or unsubstituted. Where substituted, there will generally be 1 to 3 substituents present, preferably 1 or 2 substituents. Substituents may include:

carbon containing groups such as
  alkyl
  aryl, arylalkyl  (e.g. substituted and unsubstituted phenyl, substituted and unsubstituted benzyl);
halogen atoms and halogen containing groups such as
  haloalkyl  (e.g. trifluoromethyl);
oxygen containing groups such as
  alcohols  (e.g. hydroxy, hydroxyalkyl, (aryl)(hydroxy)alkyl),
  ethers  (e.g. alkoxy, alkoxyalkyl, aryloxyalkyl),
  oxo
  aldehydes  (e.g. carboxaldehyde),
  ketones  (e.g. alkylcarbonyl, alkylcarbonylalkyl, arylcarbonyl, arylalkylcarbonyl, arylcarbonylalkyl),
  acids  (e.g. carboxy, carboxyalkyl),
  acid derivatives such as esters
    (e.g. alkoxycarbonyl, alkoxycarbonylalkyl, alkycarbonylyoxy, alkycarbonylyoxyalkyl)
    and amides
    (e.g. aminocarbonyl, mono- or di-alkylaminocarbonyl, aminocarbonylalkyl, mono- or di-alkylaminocarbonylalkyl, arylaminocarbonyl);
nitrogen containing groups such as -continued

| | |
|---|---|
| amines | (e.g. amino, mono- or di-alkylamino, aminoalkyl, mono- or di-alkylaminoalkyl), |
| azides, | |
| nitriles | (e.g. cyano, cyanoalkyl), |
| nitro; | |
| sulphur containing groups such as | |
| thiols, thioethers, sulphoxides and sulphones | |
| | (e.g. alkylthio, alkylsulfinyl, alkylsufonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); |
| and heterocyclic groups containing one or more, preferably one, heteroatom, | |
| | (e.g. thienyl, furanyl, pyrrolyl, imidazolyl, pyrazolyl, thiazolyl, isothiazolyl, oxazolyl, pylrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxylndolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl). |

Preferred substituents include alkyl, aryl, halo, or an halogen-containing group such as trifluoromethyl.

As used herein, the term "alkoxy" means alkyl-O— and "alkoyl" means alkyl-CO—.

As used herein, the term "halogen" means a fluorine, chlorine, bromine or iodine radical, preferably a fluorine or chlorine radical.

The compounds of formula (1) may exist in a number of diastereomeric and/or enantiomeric forms. Reference in the present specification to "a compound of formula (1)" is a reference to all stereoisomeric forms of the compound and includes a reference to the unseparated stereoisomers in a mixture, racemic or non-racemic, and to each stereoisomer in its pure form.

In the compounds of formula (1), preferably $R^1$ is a substituted or unsubstituted aryl group selected from phenyl, naphthyl and indanyl, more preferably $R^1$ is a substituted phenyl, naphthyl or indanyl, more preferably $R^1$ is a phenyl, naphthyl or indanyl having 1 to 3 substituents and, more preferably, $R^1$ is a phenyl, naphthyl or indanyl having 1 or 2 substituents. It is preferred that $R^1$ is a mono- or di-substituted phenyl or naphthyl, preferably a mono- or di-substituted phenyl, and most preferably a mono-substituted phenyl.

Where $R^1$ is a phenyl having 1 substituent, the phenyl group is preferably meta- or para-substituted. Where $R^1$ is a phenyl having 2 substituents, the phenyl group is preferably a 3,4-disubstituted phenyl or a 3,5-disubstituted phenyl, more preferably a 3,4-disubstituted phenyl.

Where $R^1$ is a naphthyl group it is preferred that $R^1$ is a 2-naphthyl group. Where $R^1$ is an indanyl group, it is preferred that $R^1$ is a 5-indanyl group.

Where $R^1$ is substituted, the preferred substituents are selected from chloro, fluoro, bromo, iodo, trifluoromethyl, tertiary-butyl, phenyl, $CO_2Me$ and CN, preferably from chloro, fluoro, trifluoromethyl and tertiary-butyl, and more preferably from chloro, trifluoromethyl and tertiary-butyl.

Where $R^1$ is di-substituted, it is preferred that each substituent is independently selected from halo, preferably chloro and fluoro. Where $R^1$ is di-substituted, it is preferred that $R^1$ is substituted by two chloro groups or by one chloro and one fluoro group, and more preferably by two chloro groups.

The most preferred $R^1$ groups are selected from 3-chlorophenyl, 4-chlorophenyl, 4-fluorophenyl, 4-tert-butylphenyl, 4-(trifluoromethyl)phenyl, 3-(trifluoromethyl)phenyl, 3,4-dichlorophenyl and 3,5-dichlorophenyl.

In the compounds of formula (1), $R^2$ is selected from H, alkyl (including hydroxyalkyl such as $CH_2OH$) and aryl. Preferably $R^2$ is selected from H and alkyl. Where $R^2$ is alkyl, $R^2$ is preferably methyl. Where $R^2$ is aryl, $R^2$ is preferably phenyl. Preferably $R^2$ is H or methyl. More preferably $R^2$ is methyl.

In the compounds of formula (1), $R^3$ is selected from H, alkyl (including hydroxyalkyl such as $CH_2OH$) and aryl. Preferably $R^3$ is selected from H and alkyl. Where $R^3$ is alkyl, $R^3$ is preferably methyl. Where $R^3$ is aryl, $R^3$ is preferably phenyl. Preferably $R^3$ is H or methyl.

In the compounds of formula (1), preferably $R^4$ is selected from H and alkyl (including hydroxyalkyl). Preferably $R^4$ is H or methyl. More preferably $R^4$ is H.

In the compounds of formula (1), preferably $R^5$ is selected from H and alkyl (including carboxy, alkoxycarbonyl and aminocarbonyl). $R^5$ is preferably H or methyl. More preferably $R^5$ is H.

In the compounds of formula (1), preferably $R^6$ is selected from H and alkyl (including carboxy, alkoxycarbonyl and aminocarbonyl). $R^6$ is preferably H or methyl. More preferably $R^6$ is H.

In one embodiment of the invention $R^2$, $R^3$, $R^4$, $R^5$ and $R^6$ are independently selected from H and alkyl.

In a further embodiment of the invention, $R^2$ is H and $R^3$ is methyl or $R^2$ is methyl and $R^3$ is H.

In a further embodiment of the invention $R^4$, $R^5$ and $R^6$ are H.

In the compounds of formula (1), $R^2$ and $R^4$ may optionally be linked by a saturated divalent radical chain of carbon atoms to form a 5, 6 or 7 membered ring, preferably a 5 membered ring, such as tetrahydrofuran.

In the compounds of formula (1), $R^2$ and $R^3$ may optionally be linked by a saturated divalent radical chain of carbon atoms to form a 5, 6 or 7 membered ring, preferably a 6 membered ring, such as cyclohexane.

In the compounds of formula (1), $R^2$ and $R^5$ may optionally be linked by a saturated divalent radical chain of carbon atoms to form a 5, 6 or 7 membered ring, preferably a 6 membered ring, such as cyclohexane.

Particularly preferred compounds are as follows:

| Chirality | $R^1$ | $R^2$ | $R^3$ | $R^4$ | $R^5$ | $R^6$ |
|---|---|---|---|---|---|---|
| R | 4-$(Me_3C)$—$C_6H_4$ | H | Me | H | H | H |
| R | 4-Cl—$C_6H_4$ | H | Me | H | H | H |
| S | 4-Cl—$C_6H_4$ | Me | H | H | H | H |
| — | 4-Cl—$C_6H_4$ | Me | Me | H | H | H |
| R | 4-F—$C_6H_4$ | H | Me | H | H | H |
| R | 3,4-$Cl_2$—$C_6H_3$ | H | Me | H | H | H |
| R | 4-$CF_3$—$C_6H_4$ | H | Me | H | H | H |
| R | 3-$CF_3$—$C_6H_4$ | H | Me | H | H | H |
| R | 3-Cl—$C_6H_4$ | H | Me | H | H | H |
| R | 3,5-$Cl_2$—$C_6H_3$ | H | Me | H | H | H |

Of these, the preferred compounds are: (R)-3-(4tert-butylphenoxy)-N-(2-hydroxypropyl)azetidine-1-carboxamide, (R)-3-(4-chlorophenoxy)-N-(2-hydroxypropyl)azetidine-1-carboxamide, (S)-3-(4-chlorophenoxy)-N-(2-hydroxypropyl)azetidine-1-carboxamide, (R)-3-(3,4-dichlorophenoxy)-N-(2-hydroxypropyl)azetidine-1-carboxamide, (R)-3-(4-trifluoromethyl)phenoxy-N-(2-hydroxypropyl)azetidine-1-carboxamide and (R)-3-(3-trifluoromethyl)phenoxy-N-(2-hydroxypropyl)azetidine-1-carboxamide.

The compounds of the present invention, particularly those compounds in which $R^4$ is hydrogen, are more water soluble than the compounds previously used as anxiolytic or anti-epileptic agents. A further advantage of the compounds of the present invention is the presence of a hydroxyl group which provides an available functionality for subsequent derivatisation for the further modification of physical and chemical properties.

According to a further aspect of the present invention there is provided a compound according to the present invention for use in therapy.

The compounds of the present invention may be used in the treatment (including prophylaxis) of CNS disorders. In particular, the compounds of the present invention may be used in the treatment (including prophylaxis) of anxiety, epilepsy, insomnia, including travel insomnia and insomnia associated with terminal illness, alcohol withdrawal syndrome, chronic and acute pain, neurodegenerative diseases (for example, senile dementia) and symptoms related to withdrawal from substance abuse. The compounds may also be used in the relief of spasticity. The compounds of the present invention may also be used in muscle relaxation prior to surgery or surgical manipulation or as pre-medication prior to surgery..

In a preferred embodiment of the present invention, the compounds are used in the treatment (including prophylaxis) of anxiety or epilepsy.

Anxiety includes generalised anxiety disorder (GAD), panic disorder, panic disorder plus agoraphobia, simple (specific) phobias (e.g. arachnophobia, performance anxiety such as public speaking), social phobias, post-traumatic stress disorder, anxiety associated with depression, and obsessive compulsive disorder (OCD).

Epilepsy is a chronic disorder characterised by recurrent seizures. Two forms of epilepsy exist—partial and generalised epilepsy—and each type is subdivided into idiopathic (cause unknown) or symptomatic (cause known). There are two fundamental types of seizures: partial seizures which includes simple partial seizures, complex partial seizures, and partial seizures secondarily generalised; and generalised seizures which includes generalised tonic-clonic seizures (grand mal), absence seizures (petit mal), myoclonic seizures, atonic seizures, clonic seizures, and tonic seizures.

According to a further aspect of the present invention there is provided use of a compound of the present invention in the manufacture of a medicament for the treatment (including prophylaxis) of CNS disorders, preferably anxiety, epilepsy, insomnia, including travel insomnia and insomnia associated with terminal illness, alcohol withdrawal syndrome, chronic and acute pain, neurodegenerative diseases, symptoms relating to withdrawal from substance abuse or spasticity, and more preferably anxiety or epilepsy.

According to a further aspect of the present invention there is provided use of a compound of the present invention in the manufacture of a medicament for muscle relaxation prior to surgery or surgical manipulation or as pre-medication prior to surgery.

The invention further provides a method of treatment (including prophylaxis) of CNS disorders, preferably anxiety, epilepsy, insomnia, including travel insomnia and insomnia associated with terminal illness, alcohol withdrawal syndrome, chronic and acute pain, neurodegenerative diseases, symptoms relating to withdrawal from substance abuse and spasticity, and more preferably anxiety or epilepsy, comprising administering to a patient in need of such treatment an effective dose of a compound according to the present invention.

The invention further provides a method of muscle relaxation prior to surgery or surgical manipulation or as pre-medication prior to surgery, comprising administering to a patient in need thereof an effective dose of a compound according to the present invention.

According to a further aspect of the present invention there is provided a method of preparing a compound of the present invention.

Compounds of the invention may be prepared according to the reaction scheme (where P is a nitrogen protecting group). $R^1$, $R^2$, $R^3$, $R^4$, $R^5$, $R^6$ are as previously defined. The 3-(aryloxy)azetidine (III) may be formed by reaction of the azetidinol (II) either with an arylalkanol ($R^1OH$) and diethylazo dicarboxylate and triphenyl phosphine or with a substituted aryl fluoride ($R^1F$) and a strong base such as sodium hydride. Formation of the azetidine (IV) is achieved by reaction of (III) with a suitable nitrogen deprotection agent. For example, if P is a diphenylmethyl group, then deprotection may be carried out by treatment with 1-chloroethyl chloroformate followed by methanol. The urea (I) is formed by reaction of azetidine (IV) with an N-alkylisocyanate or an N-alkylcarbamoyl chloride and a base such as triethylamine or potassium carbonate. Alternatively, the urea may be prepared directly from the azetidine (III) without isolation of an intermediate such as the secondary amine (IV). For example, when P is a diphenylmethyl group, azetidine (III) may be treated with phosgene followed by alkylamine $R^4O.CR^2R^3.CR^5R^6.NH_2$ to give urea (I) directly.

Reaction Scheme

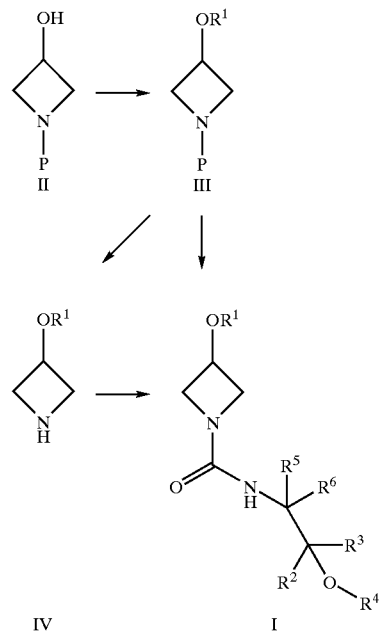

The invention further provides a pharmaceutical composition comprising a compound according to the present invention in combination with a pharmaceutically acceptable carrier or excipient and a method of making such a composition comprising combining a compound according to the present invention with a pharmaceutically acceptable carrier or excipient.

Compounds of the present invention may be administered in a form suitable for oral use, for example a tablet, capsule, aqueous or oily solution, suspension or emulsion; for topical use including transmucosal and transdermal use, for example a cream, ointment, gel, aqueous or oil solution or suspension, salve, patch or plaster, for nasal use, for a example a snuff, nasal spray or nasal drops; for vaginal or rectal use, for example a suppository; for administration by inhalation, for example a finely divided powder or a liquid aerosol; for sub-lingual or buccal use, for example a tablet or capsule; or for parenteral use (including intravenous, subcutaneous, intramuscular, intravascular or infusion), for example a sterile aqueous or oil solution or suspension. In general the above compositions may be prepared in a conventional manner using conventional excipients, using standard techniques well known to those skilled in the art of pharmacy. Preferably, the compound is administered orally.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

It will be appreciated that the dosage levels used may vary over quite a wide range depending upon the compound used, the severity of the symptoms exhibited by the patient and the patient's body weight.

The invention will now be described in detail with reference to the following examples. It will be appreciated that the invention is described by way of example only and modification of detail may be made without departing from the scope of the invention.

Experimental

Antagonism of 3-MPA-Induced Seizures

Several animal seizure models are available for the screening and characterisation of anticonvulsant (antiepileptic) drugs. Most models employ a chemical convulsant to induce seizures and the anticonvulsant potencies of novel compounds are measured in terms of their ability to increase the dose of convulsant required to induce a seizure response (or to prolong the latency to seizure onset following a bolus dose of the convulsant). Most chemical convulsants work by blocking the neurotransmitter function of gamma-aminobutyric acid (GABA), the predominant inhibitory neurotransmitter in the mammalian brain. This can be achieved by blocking the postsynaptic action of GABA using pentylenetetrazol or bicuculline, or via a presynaptic action using a GABA synthesis inhibitor to decrease GABA release into the synapse. In this case, the inhibitor of glutamate decarboxylase (GAD), 3-mercaptopropionic acid (3-MPA), was used as the convulsant challenge agent. Anticonvulsant effects of test compounds were determined by their abilities to significantly increase the dose of 3-MPA required to initiate a seizure response.

Male albino T/O strain mice (obtained from Tuck) weighing 28–40 g were used in these studies. Animals were assigned randomly to treatment groups and vehicle or test drug (at a dose of 30 ng/kg) were administered p.o. to groups of 12 animals 60 min before the administration of a bolus dose of 3-MPA intravenously. Immediately following 3-MPA administration, each mouse was placed individually into a cage for observation. The seizure response of each animal was scored quantally as present or absent (response or non-response) during the 5 min period immediately following 3-MPA administration. A seizure response was defined as the onset of the initial clonic phase of the seizure (abrupt loss of righting reflex accompanied by vocalisation). The seizure threshold (in terms of mg/kg i.v. of 3-MPA required to evoke a seizure response) was determined in each treatment group by a sequential up/down method followed by modified probit analysis of the quantal data A range of doses of 3-MPA was prepared (12.5–200.0 mg/kg i.v.) increasing by a constant geometric factor ($^3\sqrt{2}$), which was found in pilot studies to generate suitable data for analysis by this method.

In these studies, 3-MPA was obtained from Sigma

Test compounds were prepared as solutions dissolved in 45% w/v aqueous 2-hydroxypropyl-$\beta$-cyclodextrin. 3-MPA was dissolved in isotonic saline and its pH adjusted to 6 using 1M sodium hydroxide solution. Drugs were administered in a dose volume of 10 ml/kg body weight. The results are shown in Table 1.

TABLE 1

Antagonism of 3-MPA-Induced Seizures: Results of Testing

| Compound | SC | SV |
| --- | --- | --- |
| Example 1 | 154.3 | 17.7 |
| Example 2 | 109.1 | 17.7 |
| Example 3 | 59.5 | 18.3 |
| Example 4 | 36.9 | 14.9 |
| Example 5 | 29.8 | 14.9 |
| Example 6 | 59.5 | 17.7 |
| Example 8 | 214.1 | 13.2 |

SC = seizure threshold after treatment with test drug
SV = seizure threshold in vehicle-treated group Measurement of Anxiolytic Activity in Mice Using the Elevated Zero-maze Model The elevated "zero-maze" is a modification of the elevated plus-maze model of anxiety which incorporates both traditional and novel ethological measures in the analysis of drug effects (Shepherd, J. K., Grewal, S. S., Fletcher, A., Bill, D. J. and Dourish, C. T., Behavioural and pharmacological characterisation of the elevated "zero-maze" as an animal model of anxiety. *Psychopharmacology*, 1994, 116, 56–64).

Male Sprague-Dawley rats (Charles River) weighing 300–450 gm are used. Animals are group-housed (5 per cage; cage size: 40×40×20 cm) in a temperature-controlled environment (20±2° C.), under a 12 h light-dark cycle (lights on: 08:00 hours). Food and water are made freely available. Four hours prior to testing, animals are transferred to clean cages and moved to the testing room in order to habituate to the testing environment.

The maze is comprised of a black Perspex annular platform (105 cm diameter, 10 cm width) elevated to 65 cm above ground level, divided equally into four quadrants. Two opposite quadrants are enclosed by clear red Perspex walls (27 cm high) on both the inner and outer edges of the platform, while the remaining two opposite quadrants are surrounded only by a Perspex "lip" (1 cm high) which serves as a tactile guide to animals on these open areas. To facilitate the measurement of locomotor activity, the apparatus is divided into octants by splitting each quadrant into equal halves using high contrast white lines. The apparatus is illuminated by dim red lighting arranged in such a manner as to provide similar lux levels in both the open and closed quadrants (40–60 lux). A video camera, connected to a VCR in an adjacent observation room, is mounted overhead in order to record behaviour on the maze for subsequent analysis.

Chlordiazepoxide hydrochloride [CDP; Sigma Chemical Co. Ltd,. Poole], which has previously been shown to display robust anxiolytic-like effects in the zero-maze, serves as positive control. Drugs are typically dissolved in a 45% solution of 2-hydroxypropyl-β-cyclodextrin, and administered orally by gavage 1 hour prior to zero-maze testing.

Rats are placed on a closed quadrant and a 5 min test period is recorded on video-tape. The maze is cleaned with a 5% methanol/water solution and dried thoroughly between test sessions. Five behavioural parameters are scored: [1] percentage of time spent on the open areas; [2] frequency of head dips over the edge of the platform when subjects are located in either the open or the end of the closed quadrants; [3] frequency of stretch-attend postures (SAP) from closed to open quadrants, determined when the subject, on a closed quadrant, exhibits an elongated body posture stretched forward with at least the snout passing over the open/close divide; [4] frequency of rearing; and [5] the number of line crossings. Animals are scored as being in the open area when all four paws were in an open quadrant, and in the closed area only when all four paws passed over the open/closed divide. All testing is carried out between 1100 and 1700 hours.

An increase in the frequency of head dips is considered to be a measure of anxiolytic activity. The compound of example 7 was found to be effective at a dose of 30 mg/Kg.

TABLE 2

Solubility Measurement

| Compound | Aqueous solubility at 1 mg/ml |
|---|---|
| Example 2 | Soluble |
| 3-(4-chlorophenoxy)-N-(propyl)azetidine-1-carboxamide | Not soluble |
| 3-(4-chlorophenoxy)azetidine-1-carboxamide | Not soluble |
| Example 8 | Soluble |
| 3-(4-(trifluoromethyl)phenoxy)-N-(2-propenyl)azetidine-1-carboxamide | Not soluble |

Chemistry

Preparation of 1-(Diphenylmethyl)-3-azetidinol

This compound was prepared according to the method of Anderson and Lok (*J. Org. Chem.*, 1972, 37, 3953, the disclosure of which is incorporated herein by reference), m.p. 111–112° C. (lit. m.p. 113° C.).

Preparation of 3-(4-tert-Butylphenoxy)-1-(diphenylmethyl)azetidine (1)

Triphenylphosphine (13.11 g, 50.0 mmol) was added to a stirred solution of 1-(diphenylmethyl)-3-azetidinol (11.97 g, 50.0 mmol) and 4-tert-butylphenol (7.50 g, 50.0 mmol) in acetonitrile (200 mL). Diethyl azodicarboxylate (7.9 mL, 8.7 g, 50.0 mmol) was added dropwise to the solution with water cooling. The suspension was heated under reflux for 4 h, the solution allowed to cool and concentrated in vacuo. The gum was suspended in ether (200 mL), and the suspension was refrigerated overnight. The precipitated triphenylphosphine oxide was filtered off and washed with ether, and the combined filtrate and washings were concentrated. The solid residue was dissolved in dichloromethane (200 mL), and the solution was washed with 1-N sodium hydroxide (50 mL), dried ($Na_2SO_4$), and concentrated in vacuo. The crude product was purified by chromatography [$SiO_2$; ethyl acetate-hexane (1:4)] and triturated with cyclohexane to give the title compound (9.39 g, 51%) as a white solid, m.p. 126–127° C. Found: C, 83.9; H, 7.9; N, 3.75. $C_{26}H_{29}NO$ require C, 84.1; H, 7.9; N, 3.8%.

EXAMPLE 1

(R)-3-(4-tert-Butylphenoxy)-N-(2-hydroxypropyl)azetidine-1-carboxamide (2)

A solution of compound (1) (2.30 g, 6.19 mmol) in dichloromethane (25 mL) was treated with phosgene solution (ca. 20 wt. % in toluene; 3.28 mL, 6.2 mmol) with water cooling. The solution was stirred for 1 h, cooled to 0° C., and (R)-1-amino-2-propanol (1.08 mL, 1.03 g, 13.7 mmol) added dropwise. The solution was stirred for 18 h. Dichloromethane (25 mL) was added, and the solution was washed with 1-M HCl (25 mL), dried ($Na_2SO_4$), and concentrated in vacuo. The crude product was purified by chromatography [$SiO_2$; MeOH-ethyl acetate-hexane (0:2:3→0:1:0→1:9:0)] and triturated with ether to give the title compound (1.15 g, 61%) as a white solid, m.p. 98–99° C. Found: C, 66.5; H, 8.8; N, 9.1. $C_{17}H_{26}N_2O_3$ requires C, 66.6; H, 8.55; N, 9.1%.

EXAMPLE 2

(R)-3-(4-Chlorophenoxy)-N-(2-hydroxypropyl)azetidine-1-carboxamide (3)

This product was prepared from 3-(4-chlorophenoxy)-1-(diphenylmethyl)azetidine (as described in U.S. Pat. No. 4,956,359, the disclosure of which is incorporated herein by reference) and (R)-1-amino-2-propanol using the procedure described for compound (2) (69% yield), m.p. 104–105° C. Found: C, 54.9; H, 6.0; N, 9.7. $C_{13}H_{17}N_2O_3$ requires C, 54.8; H, 6.0; N, 9.8%.

EXAMPLE 3

(S)-3-(4-Chlorophenoxy)-N-(2-hydroxypropyl)azetidine-1-carboxamide (4)

This product was prepared from 3-(4-chlorophenoxy)-1-(diphenylmethyl)azetidine and (S)-1-amino-2-propanol using the procedure described for compound (2) (57% yield), m.p. 104–105° C. Found: C, 54.7; H, 6.0; N, 9.7. $C_{13}H_{17}N_2O_3$ requires C, 54.8; H, 6.0; N, 9.8%.

EXAMPLE 4

3-(4-Chlorophenoxy)-N-(2-hydroxy-2-methylpropyl)azetidine-1-carboxamide (5)

This product was prepared from 3-(4-chlorophenoxy)-1-(diphenylmethyl)azetidine and 1-amino-2-methyl-2-propanol using the procedure described for compound (2) (35% yield), m.p. 121–122° C. Found: C, 56.0; H, 6.6; N, 8.85. $C_{14}H_{19}N_2O_3$ requires C, 56.3; H, 6.4; N, 9.4%.

EXAMPLE 5

(R)-3-(4-Fluorophenoxy)-N-(2-hydroxypropyl) azetidine-1-carboxamide (6)

This product was prepared from 3-(4-fluorophenoxy)-1-(diphenylmethyl)azetidine (as described in U.S. Pat. No. 4,956,359, the disclosure of which is incorporated herein by reference) and (R)-1-amino-2-propanol using the procedure described for compound (2) (76% yield), m.p. 112–114° C. Found: C, 58.3; H, 6.4; N, 10.4. $C_{13}H_{17}FN_2O_3$ requires C, 58.2; H, 6.4; N, 10.4%.

EXAMPLE 6

(R)-3-(3,4-Dichlorophenoxy)-N-(2-hydroxypropyl) azetidine-1-carboxamide (7)

This product was prepared from 3-(3,4-dichlorophenoxy)-1-(diphenylmethyl) azetidine (as described in U.S. Pat. No. 4,956,359, the disclosure of which is incorporated herein by reference) and (R)-1-amino-2-propanol using the procedure described for compound (2) (88% yield), m.p. 83–84° C. Found: C, 49.8; H, 5.05; N, 8.35. $C_{13}H_{17}N_2O_3$ requires C, 48.9; H, 5.05; N, 8.8%.

EXAMPLE 7

(R,S)-3-(4-Chlorophenoxy)-N-(2-hydroxypropyl) azetidine-1-carboximide (8)

This product was prepared from 3-(4-chlorophenoxy)-1-(diphenylmethyl)azetidine and (d,l)-1-amino-2-propanol using the procedure described for compound (2) (81% yield), m.p. 104–105° C. Found: C, 55.1; H, 6.1; N, 9.8. $C_{13}H_{17}N_2O_3$ requires C, 54.8; H, 6.0; N, 9.8%.

EXAMPLE 8

(R)-3-(4-Trifluoromethyl)phenoxy)-N-2-hydroxypropyl)azetidine-1-carboxamide (9)

This product was prepared from 3-(4-trifluoromethyl)phenoxy)-1-(diphenylmethyl)azetidine and (R)-1-amino-2-propanol using the procedure described for compound (2) (60% yield), m.p. 112.5–113° C. Found; C, 52.9; H, 5.4; N, 8.7. $C_{14}H_{17}F_3N_2O_3$ requires C, 52.8; H, 5.4; N, 8.8%.

EXAMPLES 9 TO 58

(See Table 3)

These products were prepared using the procedure described for compound (2).

TABLE 3

| Example No | Compound No | Structure | Formula |
|---|---|---|---|
| 9 | 10 | 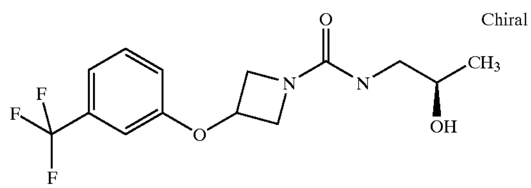 | C14H17F3N2O3 |
| 10 | 11 | 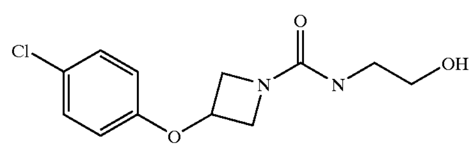 | C12H15ClN2O3 |
| 11 | 12 | 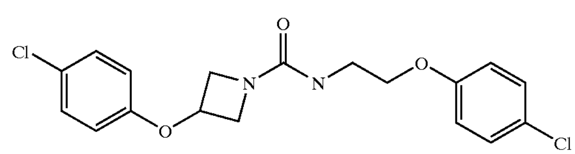 | C18H18Cl2N2O3 |
| 12 | 13 | 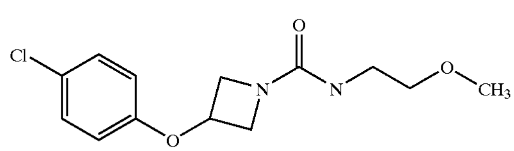 | C13H17ClN2O3 |
| 13 | 14 | 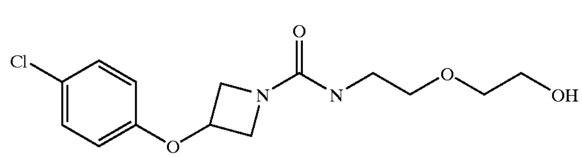 | C14H19ClN2O4 |

TABLE 3-continued

| Example No | Compound No | Structure | | Formula |
|---|---|---|---|---|
| 14 | 15 | [structure: 4-chlorophenoxy-azetidine urea with N-CH(CH3)-CH(OH)-phenyl] | Chiral | C19H21ClN2O3 |
| 15 | 16 | [structure: 4-chlorophenoxy-azetidine urea with N-CH(CH3)-CH(OH)-phenyl] | Chiral | C19H21ClN2O3 |

| Example No | Compound No | MWt | mp | Cfound | Hfound | Nfound | Cexp | Hexp | Nexp | Note |
|---|---|---|---|---|---|---|---|---|---|---|
| 9 | 10 | 318.30 | 86.00 | 52.81 | 5.34 | 8.73 | 52.83 | 5.38 | 8.80 | |
| 10 | 11 | 270.72 | | | | | | | | |
| 11 | 12 | 381.26 | | | | | | | | |
| 12 | 13 | 284.75 | | | | | | | | |
| 13 | 14 | 314.77 | | | | | | | | |
| 14 | 15 | 360.84 | | | | | | | | |
| 15 | 16 | 360.84 | | | | | | | | |

| Example No | Compound No | Structure | | Formula |
|---|---|---|---|---|
| 16 | 17 | [structure: 4-chlorophenoxy-azetidine urea with N-CH2-tetrahydrofuran-2-yl] | Chiral | C15H19ClN2O3 |
| 17 | 18 | [structure: 4-chlorophenoxy-azetidine urea with N-CH2-tetrahydrofuran-2-yl] | Chiral | C15H19ClN2O3 |
| 18 | 19 | [structure: 4-chlorophenoxy-azetidine urea with N-CH(CH3)-CH2OH] | Chiral | C13H17ClN2O3 |
| 19 | 20 | [structure: 4-chlorophenoxy-azetidine urea with N-CH(CH3)-CH2OH] | Chiral | C13H17ClN2O3 |
| 20 | 21 | [structure: 4-chlorophenoxy-azetidine urea with N-CH2-CH(OH)-phenyl] | | C18H19ClN2O3 |
| 21 | 22 | [structure: 4-chlorophenoxy-azetidine urea with N-CH2-C(OH)(cyclohexyl)] | | C17H23ClN2O3 |

TABLE 3-continued
| Example No | Compound No | Structure | | Formula |
|---|---|---|---|---|
| 22 | 23 | 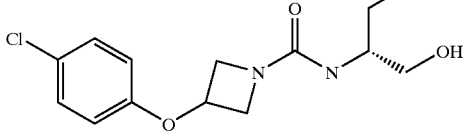 | Chiral | C14H19ClN2O3 |
| Example No | Compound No | MWt | mp | Cfound | Hfound | Nfound | Cexp | Hexp | Nexp | Note |
|---|---|---|---|---|---|---|---|---|---|---|
| 16 | 17 | 310.78 | | | | | | | | |
| 17 | 18 | 310.78 | | | | | | | | |
| 18 | 19 | 284.75 | | | | | | | | |
| 19 | 20 | 284.75 | | | | | | | | |
| 20 | 21 | 346.82 | | | | | | | | |
| 21 | 22 | 338.84 | | | | | | | | |
| 22 | 23 | 298.77 | | | | | | | | |
| Example No | Compound No | Structure | Formula |
|---|---|---|---|
| 23 | 24 | 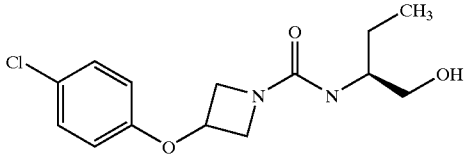 Chiral | C14H19ClN2O3 |
| 24 | 25 | 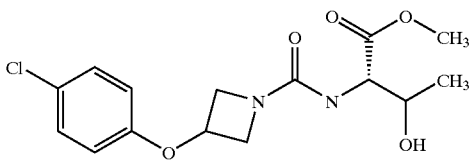 Chiral | C15H19ClN2O5 |
| 25 | 26 | 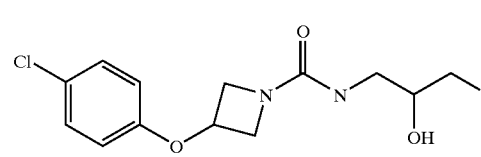 | C13H17ClN2O4 |
| 26 | 27 | 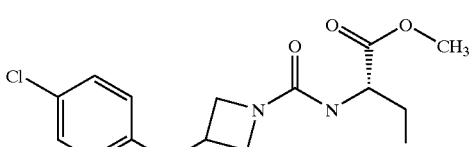 Chiral | C14H17ClN2O5 |
| 27 | 28 | 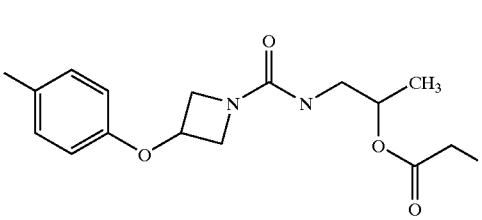 | C17H24ClN3O4 |
| 28 | 29 | 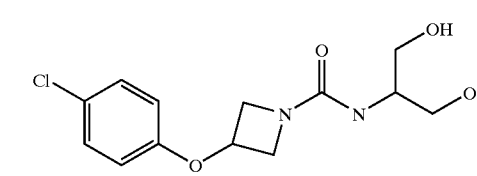 | C13H17ClN2O4 (0.5 H2O) |

TABLE 3-continued
| Example No | Compound No | Structure | | Formula |
|---|---|---|---|---|
| 29 | 30 | 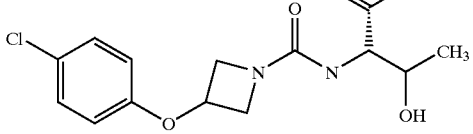 | Chiral | C14H17ClN2O5 (0.25 H2O) |
| Example No | Compound No | MWt | mp | Cfound | Hfound | Nfound | Cexp | Hexp | Nexp | Note |
|---|---|---|---|---|---|---|---|---|---|---|
| 23 | 24 | 298.77 | | | | | | | | |
| 24 | 25 | 342.78 | | | | | | | | |
| 25 | 26 | 300.74 | | | | | | | | |
| 26 | 27 | 328.75 | | | | | | | | |
| 27 | 28 | 369.85 | | | | | | | | |
| 28 | 29 | 300.74 | 119–121 | 50.60 | 5.85 | 8.97 | 50.41 | 5.86 | 9.04 | |
| 29 | 30 | 328.75 | 123–124 dec | 50.69 | 5.34 | 7.97 | 50.46 | 5.29 | 8.41 | |
| Example No | Compound No | Structure | | Formula |
|---|---|---|---|---|
| 30 | 31 | 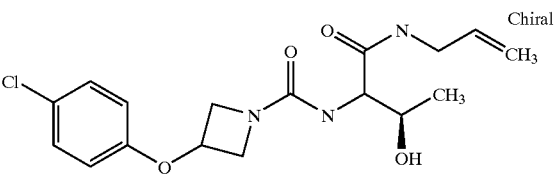 | Chiral | C17H22ClN3O4 |
| 31 | 32 | 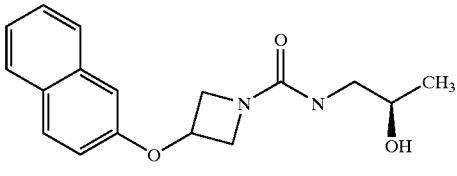 | | C17H20N2O3 |
| 32 | 33 | 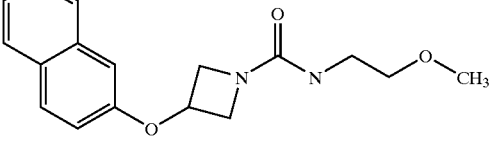 | | C17H20N2O3 |
| 33 | 34 | 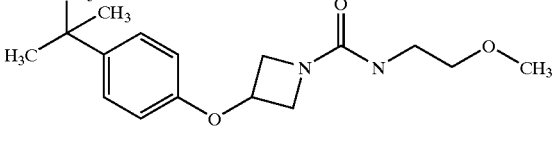 | | C17H26N2O3 |
| 34 | 35 | 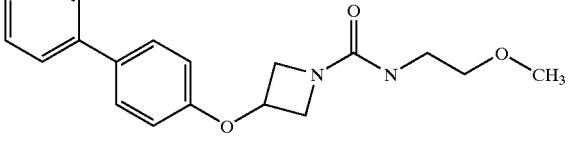 | | C19H22N2O3 |
| 35 | 36 | 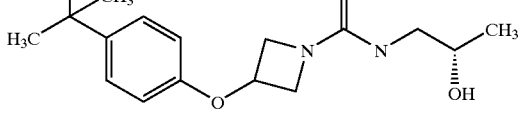 | Chiral | C17H26N2O3 |

TABLE 3-continued

| Example No | Compound No | Structure | Formula |
|---|---|---|---|
| 36 | 37 | 3,4-dichlorophenoxy-azetidine urea with (S)-2-hydroxypropyl, Chiral | C13H16Cl2N2O3 |

| Example No | Compound No | MWt | mp | Cfound | Hfound | Nfound | Cexp | Hexp | Nexp | Note |
|---|---|---|---|---|---|---|---|---|---|---|
| 30 | 31 | 367.84 | >50 dec | | | | | | | a |
| 31 | 32 | 300.36 | 136–137 | 68.03 | 6.62 | 8.76 | 67.98 | 6.71 | 9.32 | |
| 32 | 33 | 300.36 | 105–105.5 | 68.05 | 6.70 | 9.18 | 67.98 | 6.71 | 9.32 | |
| 33 | 34 | 306.41 | 97–98 | 66.75 | 8.56 | 8.81 | 66.64 | 8.55 | 9.14 | |
| 34 | 35 | 326.40 | 118.00 | 69.87 | 6.82 | 8.55 | 69.92 | 6.79 | 8.68 | |
| 35 | 36 | 306.41 | 99–100 | 66.21 | 8.55 | 9.10 | 66.64 | 8.55 | 9.14 | |
| 36 | 37 | 319.19 | 86–89 | 49.16 | 4.99 | 8.40 | 48.92 | 5.05 | 8.77 | |

| Example No | Compound No | Structure | Formula |
|---|---|---|---|
| 37 | 38 | naphthalen-2-yloxy-azetidine urea with (S)-2-hydroxypropyl, Chiral | C17H20N2O3 |
| 38 | 39 | 3,4-dichlorophenoxy-azetidine urea with 2-methoxyethyl | C13H16Cl2N2O3 |
| 39 | 40 | naphthalen-2-yloxy-azetidine urea with 2-hydroxyethyl | C16H18N2O3 |
| 40 | 41 | 4-tert-butylphenoxy-azetidine urea with 2-hydroxyethyl | C16H24N2O3 |
| 41 | 42 | biphenyl-4-yloxy-azetidine urea with (S)-2-hydroxypropyl, Chiral | C19H22N2O3 |
| 42 | 43 | 4-iodophenoxy-azetidine urea with (S)-2-hydroxypropyl, Chiral | C13H17IN2O3 |
| 43 | 44 | 4-bromophenoxy-azetidine urea with (S)-2-hydroxypropyl, Chiral | C13H17BrN2O3 |

TABLE 3-continued

| Example No | Compound No | MWt | mp | Cfound | Hfound | Nfound | Cexp | Hexp | Nexp | Note |
|---|---|---|---|---|---|---|---|---|---|---|
| 37 | 38 | 300.36 | 136–138 | 67.33 | 6.65 | 8.93 | 66.98 | 6.78 | 9.19 | |
| 38 | 39 | 319.19 | 105.5–106 | 49.04 | 4.98 | 8.60 | 48.92 | 5.05 | 8.77 | |
| 39 | 40 | 286.33 | 128–128.5 | 66.84 | 6.33 | 9.67 | 67.12 | 6.34 | 9.78 | |
| 40 | 41 | 292.38 | 111–111.5 | 65.54 | 8.34 | 9.49 | 65.73 | 8.27 | 9.58 | |
| 41 | 42 | 326.40 | 156–157 | 69.69 | 6.74 | 8.39 | 69.92 | 6.79 | 8.58 | |
| 42 | 43 | 376.20 | 118–120 | 42.18 | 4.54 | 7.21 | 41.51 | 4.55 | 7.44 | |
| 43 | 44 | 329.20 | 110–111 | 47.90 | 5.24 | 8.42 | 47.43 | 5.20 | 8.51 | |

| Example No | Compound No | Structure | Formula |
|---|---|---|---|
| 44 | 45 | 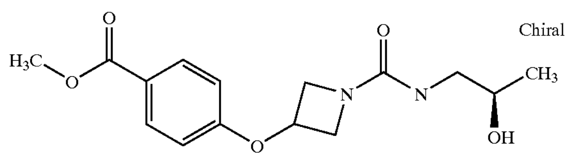 | $C_{15}H_{20}N_2O_5$ |
| 45 | 46 | 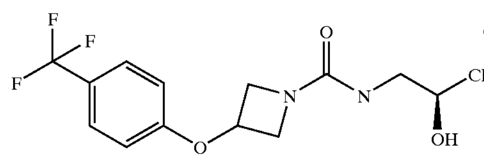 | $C_{14}H_{17}F_3N_2O_3$ |
| 46 | 47 | 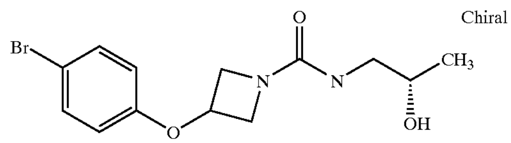 | $C_{13}H_{17}BrN_2O_3$ |
| 47 | 48 | 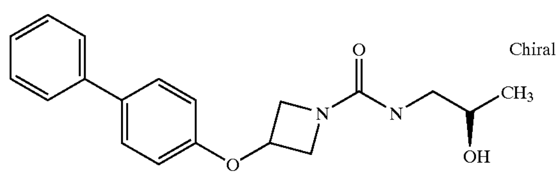 | $C_{19}H_{22}N_2O_3$ (0.25 H2O) |
| 48 | 49 | 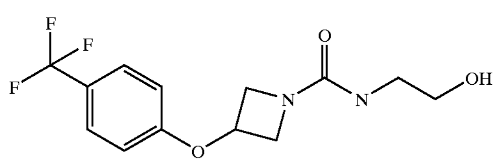 | $C_{13}H_{15}F_3N_2O_3$ |
| 49 | 50 | 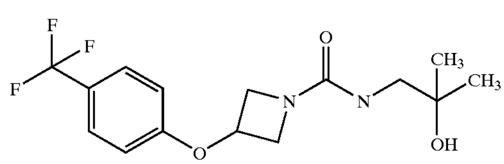 | $C_{15}H_{19}F_3N_2O_3$ |
| 50 | 51 | 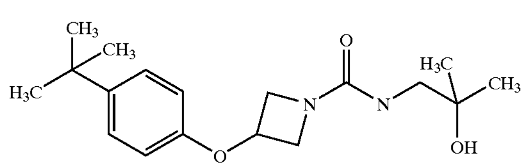 | $C_{18}H_{28}N_2O_3$ |

| Example No | Compound No | MWt | mp | Cfound | Hfound | Nfound | Cexp | Hexp | Nexp | Note |
|---|---|---|---|---|---|---|---|---|---|---|
| 44 | 45 | 308.34 | 243–244 | 58.46 | 6.56 | 9.05 | 58.43 | 6.54 | 9.08 | |
| 45 | 46 | 318.30 | 111–111.5 | 53.09 | 5.46 | 8.72 | 52.81 | 5.38 | 8.80 | |

TABLE 3-continued

| | | | | | | | | | |
|---|---|---|---|---|---|---|---|---|---|
| 46 | 47 | 329.20 | 108–110 | 48.09 | 5.18 | 8.16 | 47.43 | 5.20 | 8.51 |
| 47 | 48 | 326.40 | 157–158 | 69.19 | 6.84 | 8.65 | 68.97 | 6.85 | 8.47 |
| 48 | 49 | 304.27 | 113.5–114.5 | 51.37 | 5.01 | 9.06 | 51.32 | 4.97 | 9.20 |
| 49 | 50 | 332.33 | 136–137 | 54.09 | 5.94 | 8.40 | 54.21 | 5.76 | 8.43 |
| 50 | 51 | 320.44 | 104.5–106 | 67.36 | 9.04 | 8.73 | 67.47 | 8.81 | 8.74 |

| Example No | Compound No | Structure | Formula |
|---|---|---|---|
| 51 | 52 | (3,5-dichlorophenoxy-azetidine urea with chiral 2-hydroxypropyl), Chiral | C13H16Cl2N2O3 |
| 52 | 53 | (4-chlorophenoxy-azetidine urea with 2-methyl-2-hydroxymethyl) | C14H19ClN2O3 (0.5 H2O) |
| 53 | 54 | (4-chlorophenoxy-azetidine urea with trans-2-hydroxycyclohexyl) | C16H21ClN2O3 |
| 54 | 55 | (4-chloro-3-fluorophenoxy-azetidine urea with chiral 2-hydroxypropyl), Chiral | C13H16ClFN2O3 |
| 55 | 56 | (4-ethynylphenoxy-azetidine urea with 2-hydroxypropyl) | C14H17N3O3 |
| 56 | 57 | (indanyloxy-azetidine urea with 2-hydroxypropyl) | C16H22N2O3 |
| 57 | 58 | (3-trifluoromethylphenoxy-azetidine urea with chiral 2-hydroxypropyl), Chiral | C14H17F3N2O3 |

| Example No | Compound No | MWt | mp | Cfound | Hfound | Nfound | Cexp | Hexp | Nexp | Note |
|---|---|---|---|---|---|---|---|---|---|---|
| 51 | 52 | 319.19 | 121–121.5 | 48.97 | 4.98 | 8.87 | 48.92 | 5.05 | 8.77 | |
| 52 | 53 | 298.77 | 153.00 | 54.69 | 6.28 | 9.26 | 54.63 | 6.55 | 9.10 | |
| 53 | 54 | 324.81 | 154–155.5 | 59.12 | 6.58 | 8.64 | 59.17 | 6.52 | 8.62 | |
| 54 | 55 | 302.74 | 118.5–120.5 | 51.62 | 5.37 | 9.14 | 51.58 | 5.33 | 9.25 | |
| 55 | 56 | 275.31 | | | | | | | | b |
| 56 | 57 | 290.37 | | | | | | | | c |
| 57 | 58 | 318.30 | | 52.91 | 5.42 | 8.72 | 52.83 | 5.38 | 8.80 | |

TABLE 3-continued

| Example No | Compound No | Structure | Formula |
|---|---|---|---|
| 58 | 59 | 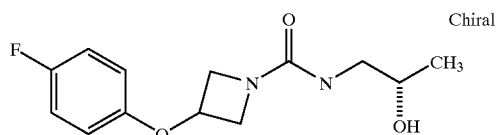 Chiral | C13H17FN2O3 |

| Example No | Compound No | MWt | mp | Cfound | Hfound | Nfound | Cexp | Hexp | Nexp | Note |
|---|---|---|---|---|---|---|---|---|---|---|
| 58 | 59 | 268.29 | | 58.31 | 6.44 | 10.39 | 58.20 | 6.39 | 10.44 | |

What is claimed is:

1. A compound of formula (1)

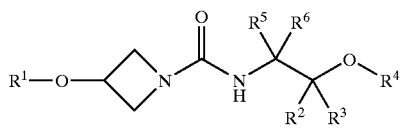 (1)

wherein $R^1$ is aryl; and $R^2$, $R^3$, $R^4$, $R^5$ and $R^6$ which may be the same or different are selected from H, alkyl and aryl;

and pharmaceutically acceptable addition compounds thereof.

2. A compound according to claim 1 wherein $R^1$ is a substituted or unsubstituted aryl group selected from phenyl, naphthyl and indanyl.

3. A compound according to claim 1 wherein $R^1$ has 1, 2 or 3 substituent groups.

4. A compound according to claim 1 wherein $R^1$ is a para-substituted phenyl group.

5. A compound according to claim 1 wherein $R^1$ is a meta-substituted phenyl group.

6. A compound according to claim 1 wherein $R^1$ is a 3,4-disubstituted phenyl group or a 3,5-disubstituted phenyl group.

7. A compound according to claim 1 wherein $R^1$ is substituted by one or more groups selected from chloro, fluoro, bromo, iodo, trifluoromethyl, tertiary-butyl, phenyl, $CO_2Me$ and CN.

8. A compound according to claim 1 wherein $R^1$ is selected from 3-chlorophenyl, 4-chlorophenyl, 4-fluorophenyl, 4-tert-butylphenyl, 4-(trifluoromethyl) phenyl and 3-(trifluoromethyl)phenyl.

9. A compound according to claim 1 wherein $R^1$ has 2 substituent groups each of which are independently selected from halo.

10. A compound according to claim 1 wherein $R^1$ is 3,4-dichlorophenyl, 3-chloro-4-fluorophenyl, 4-chloro-3-fluorophenyl or 3,5-dichlorophenyl.

11. A compound according to claim 1, wherein $R^2$, $R^3$, $R^4$, $R^5$ and $R^6$ are independently selected from H and alkyl.

12. A compound according to claim 1, wherein $R^2$, $R^3$, $R^4$, $R^5$ and $R^6$ are independently selected from H and methyl.

13. A compound according to claim 1 wherein one or both of $R^2$ and $R^3$ are hydroxyalkyl.

14. A compound according to claim 1 wherein one or both of $R^2$ and $R^3$ are phenyl.

15. A compound according to claim 1 wherein $R^4$ is hydroxyalkyl.

16. A compound according to claim 1 wherein $R^5$ and $R^6$ are independently selected from carboxy, alkoxycarbonyl and aminocarbonyl.

17. A compound according to claim 1, wherein $R^4$, $R^5$ and $R^6$ are hydrogen.

18. A compound according to claim 1 wherein $R^2$ is hydrogen and $R^3$ is methyl or $R^2$ is methyl and $R^3$ is hydrogen.

19. A compound according to claim 1 wherein the compound is selected from (R)-3-(4-tert-butylphenoxy)-N-(2-hydroxypropyl)azetidine-1-carboxamide, (R)-3-(4-chlorophenoxy)-N-(2-hydroxypropyl)azetidine-1-carboxamide, (S)-3-(4-chlorophenoxy)-N-(2-hydroxypropyl)azetidine-1-carboxamide, 3-(4-chlorophenoxy)-N-(2-hydroxy-2-methylpropyl)azetidine-1-carboxamide, (R)-3-(4-fluorophenoxy)-N-(2-hydroxypropyl)azetidine-1-carboxamide, (R)-3-(4-trifluoromethyl)phenoxy-N-(2-hydroxypropyl)azetidine-1-carboxamide, (R)-3-(3,4-dichlorophenoxy)-N-(2-hydroxypropyl)azetidine-1-carboxamide, (R)-3-(3-trifluoromethyl)phenoxy-N-2-hydroxypropyl)azetidine-1-carboxamide, (R)-3-(3-chlorophenoxy)-N-(2-hydroxypropyl)azetidine-1-carboxamide and (R)-3-(3,5-dichlorophenoxy)-N-(2-hydroxypropyl)azetidine-1-carboxamide.

20. A compound according to claim 1, wherein $R^2$ and $R^4$ are linked by a saturated divalent radical chain of carbon atoms to form a 5, 6 or 7 membered ring.

21. A compound according to claim 1, wherein $R^2$ and $R^3$ are linked by a saturated divalent radical chain of carbon atoms to form a 5, 6 or 7 membered ring.

22. A compound according to claim 1, wherein $R^2$ and $R^5$ are linked by a saturated divalent radical chain of carbon atoms to form a 5, 6 or 7 membered ring.

23. A pharmaceutical composition comprising a compound according to claim 1 in combination with a pharmaceutically acceptable carrier or excipient.

24. A method of treatment of CNS disorders, comprising administering to a patient in need of such treatment an effective dose of a compound according to claim 1.

25. A method according to claim 24, wherein said method is for the treatment of anxiety, epilepsy, or insomnia.

26. A method according to claim 24 wherein said method is for the treatment of anxiety or epilepsy.

27. A method of muscle relaxation prior to surgery or surgical manipulation or a method of pre-medication prior to surgery, comprising administering to a patient in need thereof an effective dose of a compound according to claim 1.

28. A method according to claim 24, wherein said treatment is prophylactic.

29. A method according to claim 25, wherein said insomnia comprises travel insomnia and insomnia associated with terminal illness, alcohol withdrawal syndrome, chronic and acute pain, neurodegenerative diseases, symptoms relating to withdrawal from substance abuse or spasticity.

* * * * *